(12) United States Patent
El-Messeiry et al.

(10) Patent No.: US 10,258,807 B2
(45) Date of Patent: Apr. 16, 2019

(54) UV LIGHT THERAPY APPARATUS FOR TREATMENT OF VITAMIN D DEFICIENCY AND TO A BUILDING COMPRISING THE SAME

(71) Applicant: King Saud University, Riyadh (SA)

(72) Inventors: Mamduh A. El-Messeiry, Riyadh (SA); Abdulaziz Bin Saeed, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 13/691,921

(22) Filed: Dec. 3, 2012

(65) Prior Publication Data

US 2013/0144366 A1    Jun. 6, 2013

(30) Foreign Application Priority Data

Dec. 6, 2011 (EP) .................................. 11192135

(51) Int. Cl.
*A61N 5/06* (2006.01)

(52) U.S. Cl.
CPC ............. *A61N 5/06* (2013.01); *A61N 5/0613* (2013.01); *A61N 2005/063* (2013.01); *A61N 2005/0657* (2013.01); *A61N 2005/0661* (2013.01)

(58) Field of Classification Search
CPC ......... F21S 11/00; F21S 19/005; Y02E 10/40; A61N 2005/0657; A61N 2005/0661
See application file for complete search history.

(56) References Cited

U.S. PATENT DOCUMENTS

| | | | | |
|---|---|---|---|---|
| 4,246,477 A * | 1/1981 | Latter | ..................... | 250/214 AL |
| 5,716,442 A * | 2/1998 | Fertig | ........................... | 136/246 |
| 7,339,739 B1 * | 3/2008 | Kinney et al. | ................. | 359/591 |
| 7,973,235 B2 * | 7/2011 | Muhs et al. | ................... | 136/246 |
| 2001/0006066 A1 * | 7/2001 | Cherney et al. | ............... | 126/698 |
| 2007/0035841 A1 * | 2/2007 | Kinney | ..................... | F21S 11/00 359/592 |
| 2007/0230209 A1 | 10/2007 | Martin | | |
| 2009/0262427 A1 | 10/2009 | Whang et al. | | |
| 2010/0236626 A1 * | 9/2010 | Finot | ....................... | F24S 23/74 136/259 |
| 2011/0212410 A1 * | 9/2011 | Fiset | ............................... | 433/29 |

FOREIGN PATENT DOCUMENTS

| | | |
|---|---|---|
| CH | 307244 | 5/1955 |
| GB | 2230183 | 10/1990 |
| WO | 2008129278 | 10/2008 |

OTHER PUBLICATIONS

European Search Report for corresponding EP11192135.9 dated Mar. 6, 2012.

* cited by examiner

*Primary Examiner* — Scott Luan
(74) *Attorney, Agent, or Firm* — Renner, Otto, Boisselle & Sklar, LLP (57) ABSTRACT

Stationary UV light therapy apparatus for treatment of vitamin D deficiency, comprising: a daylight and/or sunlight collector for collecting daylight and/or sunlight over a collector square area, a light transmission component for transmitting the light collected by the collector to the interior of a room of a building, an optical filter for transmission of UV-light included in the daylight and/or sunlight, and a light distributor for distributing the UV-light over a square area of the room, wherein the square area is a part or all of the room square area and larger than the collector square area, and building comprising the same.

17 Claims, 9 Drawing Sheets

UV LIGHT THERAPY APPARATUS FOR TREATMENT OF VITAMIN D DEFICIENCY AND TO A BUILDING COMPRISING THE SAME

The present invention relates to an UV light therapy apparatus for treatment of vitamin D deficiency and to a building comprising the same.

Vitamin D is a group of fat-soluble secosteroids. In humans vitamin D is unique both because it functions as a prohormone and the body can synthesize it (as vitamin $D_3$) when sun exposure is adequate. Vitamin $D_3$ is made in the skin when 7-dehydrocholesterol reacts with ultraviolet light (UVB) at wavelengths between 270 and 300 nm, with peak synthesis occurring between 295 and 297 nm. These wavelengths are present in sunlight when the UV index is greater than three. At a UV index greater than three, which occurs daily within the tropics, daily during the spring and summer seasons in temperate regions, and almost never within the arctic circles, Vitamin $D_3$ can be made in the skin.

Vitamin D deficiency is currently recognized as a global epidemic. Vitamin D deficiency or insufficiency affects one billion people worldwide, as deduced from several studies (see for example Holick M. F.: "Vitamin D deficiency", N. Engl J. Med. 2007, vol. 3: 266-281). A major cause of vitamin D deficiency is inadequate exposure to sunlight. Dealing with the sun can be like walking a tight wire. Too much and you can get skin cancer. Too little and you can get vitamin D deficiency. Silvina Levis revealed that, while high-latitude regions are traditionally associated with inadequate levels of vitamin D, in recent years accumulating reports from various sunny countries demonstrated that this hormone insufficiency is common in tropical and subtropical regions as well (see Levis S., Gomez A., Jimenez C. et al "Vitamin D deficiency and seasonal variation in an adult South Florida population", J. Clin. Endocrinol Metab 2005, vol. 90: 1557-62). This suggests that vitamin D insufficiency is only partly explained by season and latitude. In tropic and subtopic region both men and women are keeping away from sunlight to avoid heat as their traditional dress covers the skin almost completely. The amount of time for adequate exposure depends on time of day, season, latitude, skin pigmentation, and the area of skin surface that has no sun protection (see Bill Sadir "Live longer and healthier with 30 minutes of sunshine", Knowledge of Health, Inc., 2008). Typically, the sun exposure of a person in a bathing suit of 1 minimal erythema dose is equivalent to ingesting 20.000 IU (International Unit; in pharmacology, the International Unit is a unit of measurement for the amount of a substance, based on biological activity or effect; it is abbreviated as IU and used to quantify vitamins, hormones, some medications, vaccines, blood products and similar biologically active substances) of vitamin D (about 5-15 minutes between 11 AM and 2 PM in Boston) (see Michael F. Holick "Vitamin D Deficiency: What a Pain It is", Mayo. Clin. Proc. 2003, vol. 78: 1457-1459). Some dermatologists advise that people of all ages and ethnicities should avoid all direct exposure to sunlight and should always use sun protection when being outdoors. However, a study conducted in Jordan reveals high prevalence of low vitamin D status in females in contrast with a low prevalence in males and higher prevalence in women wearing Hijab or Neqab (see Mishal, A A., "Effects of different dress styles on vitamin D levels in healthy young Jordanian women", Osteoporos Int. 2001, vol. 12: 931). People may use tanning beds to avoid exposure to direct sunlight. Indore glass windows adsorb up to 85% of ultraviolet radiation.

It is the aim of the present invitation to reduce the prevalence of vitamin D deficiency.

This aim is solved by an UV light therapy apparatus for treatment of vitamin D deficiency, comprising: a daylight and/or sunlight collector for collecting daylight and/or sunlight over a collector square area, a light transmission component for transmitting the light collected by the collector to the interior of a room of a building, an optical filter for transmission of UV-light included in the daylight and/or sunlight, and a light distributor for distributing the UV-light over a square area of the room, wherein the square area is a part or all of the room square area and larger than the collector square area.

In particular, said apparatus is a stationary apparatus.

Furthermore, said aim is solved by a building comprising at least one of the apparatus according to anyone of claims 1 to 10.

According to a particular embodiment, the collector is arranged on the roof or at the façade of the building.

Preferably the collector comprises a reflector dish antenna, preferably a multiple reflector dish antenna.

Conveniently the optical filter is arranged within the collector.

Further, the light transmission component may comprise a lightpipe, preferably a UV-lightpipe, in particular a vertical extending lightpipe, preferably extending outside of the building.

In addition, the light transmission component may comprise a deflecting means for deflecting the light, preferably in a horizontal direction.

Preferably the light distributor comprises one or more optical micro-reflectors.

According to a further special embodiment, the ratio of the collector square area and the square area is such that the UV dispersion in the room is more than about 100 times and preferably more than about 200 times less than the UV dispersion outside of the building.

Alternatively or additionally, the ratio of the collector square area and the square area is such that the UVB scale index ranges from about 0.03 to about 0.05 in the room when the UVB scale index ranges from about 6 to about 10 outside of the building. The ultraviolet index or UV index is an international standard measurement of the strength of the ultraviolet (UV) radiation from the sun at a particular place on a particular day. It is a scale primarily used in daily forecasts aimed at the general public. The UV index is a linear scale, with higher values representing the risk level of skin damage due to UV exposure. An index of 0 corresponds to zero UV irradiation, as is essentially the case at nighttime. While an index of 10 corresponds roughly to midday sun and a clear sky, indices greater than 11 are quite common in the southern hemisphere where the ozone layer is depleted. The numbers are related to the amount of UV radiation reaching the surface of the earth, measured in $W/m^2$, but the relationship is not simple, because UV power is spread unevenly over a spectrum of wavelengths. The shorter wavelengths are much more damaging. By weighting their effect the index aims to create a number that cannot be expressed in physical units, but is a good indication of likely skin damage.

Preferably the apparatus comprises a controller for controlling the UV-dosage and switching-off the UV radiation when a predetermined UV-dosage is reached.

The invention is made on the surprising findings to collect only the ultraviolet wave for transmitting it and distributing only the useful UV-part into a building at a desired level. The invention brings natural harmless light indoor at the necessary dose. The UVB scale index ranges from 1 to 13, with 1 also including all lower values, and a value of 11 or higher categorized as extreme. For example in Riyadh (Saudi Arabia), the UVB index reaches 11 at summer noon. People are trying all the time to avoid direct exposure to sunlight. Even, when women are exposed to sunlight, they are wearing Hijab or Neqab. Also men are keeping away from of sunlight to avoid heat as their traditional dress covers the skin almost completely. For example at home, school and offices where people spend most of the day, the windows are small and coated glass is installed to avoid heat. Now for example women can use the apparatus according to the present invention at their kitchen to enjoy their privacy and expose to the major cause of vitamin D and avoid heat. Also elder people will avoid osteoporosis as they stay in a room where the apparatus is installed. For example school children will beneficial avoid vitamin D deficiency while studying for long time.

Further, the present invention provides an environmental engineering tool to bring back natural ultraviolet light inside for example houses and schools to reduce the prevalence of vitamin D deficiency.

Further features and advantages of the invention will become clear from the accompanying claims as well as the following description, in which special embodiments of the invention are illustrated in detail with reference to the schematic drawings, wherein:

Figure 1:
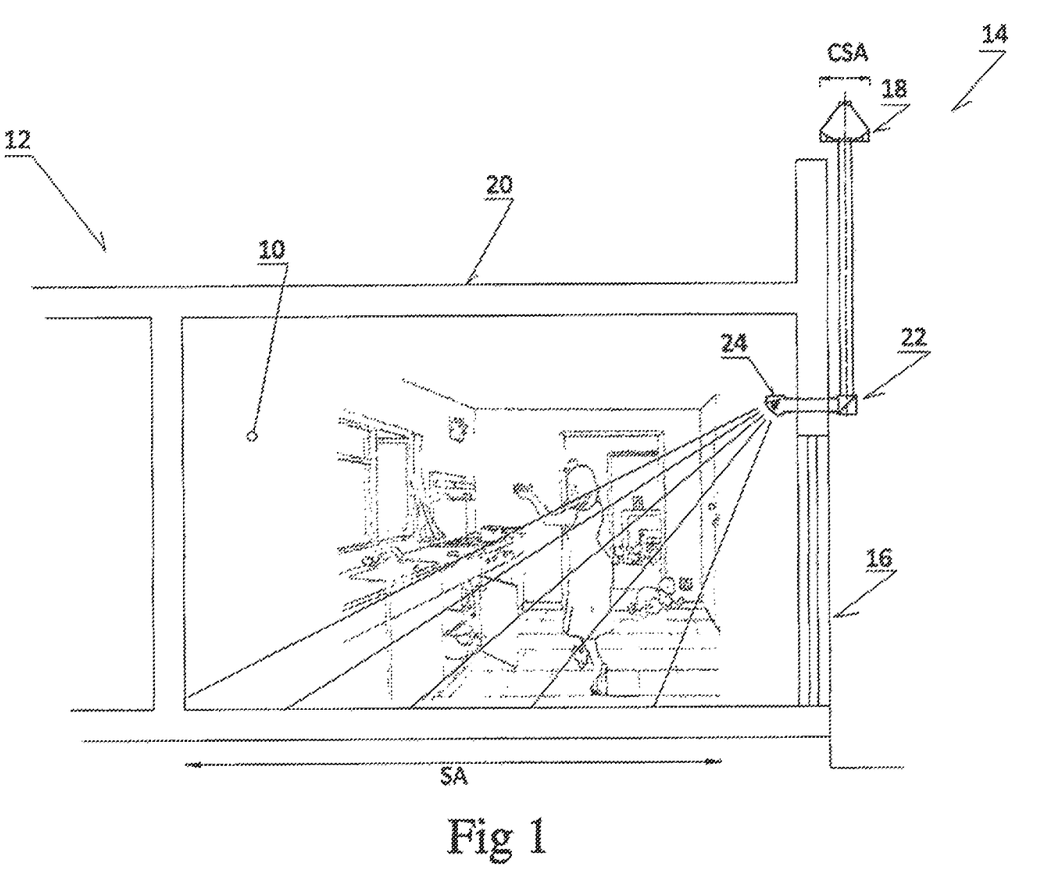
FIG. 1 shows a side view of a building comprising an UV light therapy apparatus for treatment of vitamin D deficiency according to a special embodiment of the invention, partially in section.

FIG. 1 shows a view into a room 10 of a building, namely a house 12, in particular a flat-roofed house. Said room is arranged to the outside. The house comprises an UV-light therapy apparatus 14 for treatment of vitamin D deficiency according a particular embodiment of the present invention at the façade 16 of the house 12. Said apparatus 14 comprises a daylight and/or sunlight collector 18 arranged at the façade 16 at a level that is higher than the flat-roof 20. Furthermore, said apparatus 14 comprises a light transmission component 22 for transmitting the light collected by the collector 18 to the interior of the room 10 of the house 12. Also, said apparatus 14 comprises a light distributor 24 for distributing the UV-light over a square area SA of the room 10, wherein the square area SA (4 m by 3 m=12 square meter) is all of the room square area and larger than the collector square area CSA.

Figure 2:
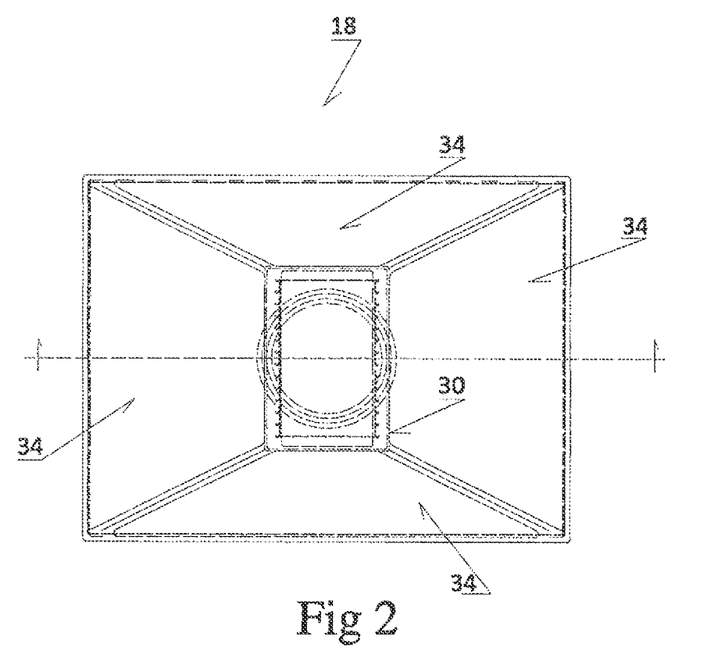
FIG. 2 shows a top view of a daylight and/or sunlight collector for collecting daylight and/or sunlight over a collector square area of the apparatus of FIG. 1.
Figure 3:
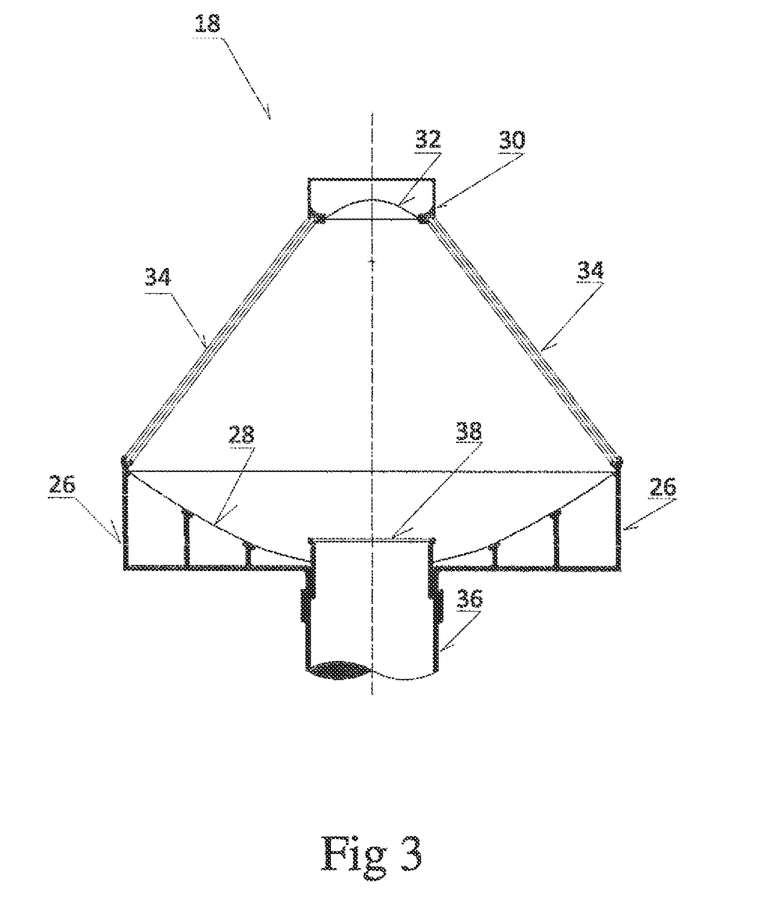
FIG. 3 shows a sectional elevation view A-A of FIG. 2.
Figure 4:
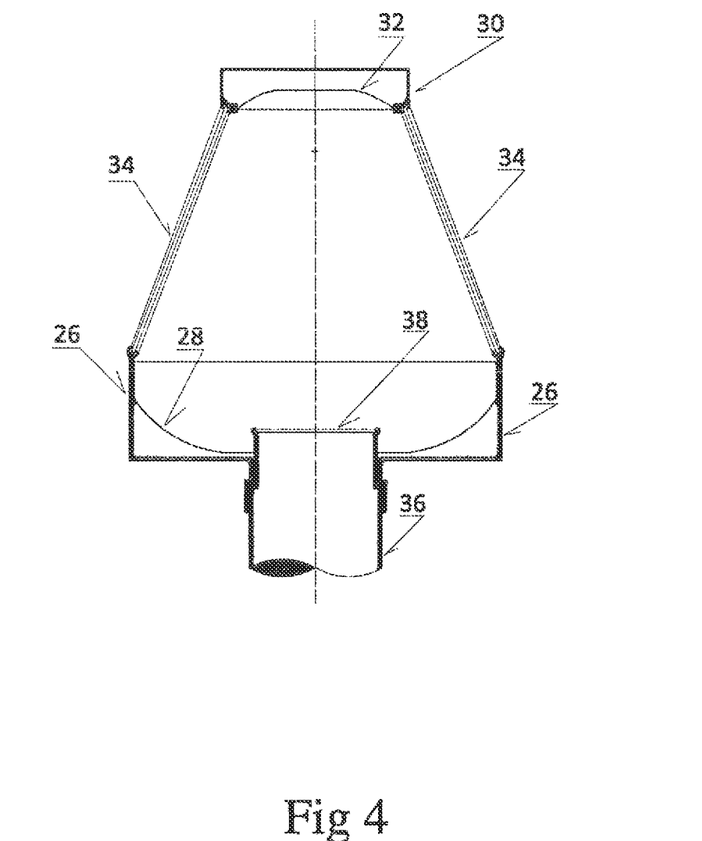
FIG. 4 shows a sectional elevation view B-B of FIG. 2.

As can be seen from FIGS. 2 to 4, the daylight and/or sunlight collector 18 comprises a bottom box 26 of aluminium with a thickness of 2 mm for holding a multiple reflector dish antenna 28 and an opposite top box 30 of aluminum with a thickness of 2 mm for holding a multiple sub reflector 32. Four transparent anti-dust-anti-fog-plastic plates 34 are arranged between the bottom box 26 and the top box 30 for covering the multiple reflector dish antenna 28 and the multiple sub reflector 32. By this, the collector 18 is essentially conically shaped.

The multiple reflector dish antenna 28 reflects daylight and/or sunlight up to the multiple sub reflector 32 to send it back to the end of a vertically extending tube 36 with a diameter of 100 mm that is arranged in the centre of a button box 26 and the multiple reflector dish antenna 28. Said tube 36 belongs to the light transmission component 22. Before entry into the end of said tube 36, the daylight and/or sunlight has to pass a visible light filter 38 with a diameter of 100 mm. So said filter 38 allows transmission of only UV-light included in the daylight and/or sunlight. In particular, the collector 18 has a height of 320 mm, a length of 404 mm and a width of 304 mm. The bottom box 26 has a rectangular basis (40 cm by 30 cm=0.12 square meter).

Figure 5:
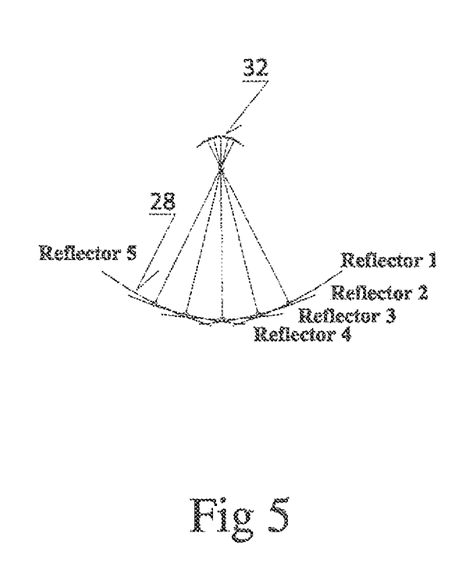
FIG. 5 shows the principle of a reflector dish antenna as part of a daylight and/or sunlight collector shown in FIGS. 2 to 4.

FIG. 5 shows details of the multiple reflector dish antenna 28, schematically consisting of reflectors 1 to 5, and of the multiple sub reflector 32, consisting of several sub reflectors. The parabolic focal length of the multiple reflector dish antenna 28 is 250 mm and its parabolic diameter is 395 mm. The parabolic focal length of the multiple sub reflector 32 is 50 mm and its parabolic diameter is 76 mm. The angle blocked by the multiple sub reflector 32 is 8° and the angle subtended by the multiple reflector dish antenna 28 is 49°. The multiple reflector dish antenna 28 can be composed of material aluminum covered by highly polished aluminum sheet in the size of 24"×48" and with a thickness 0.02" that are used for UV lamp reflectors.

The visible light filter 38 can be a glass filter (HU 02) that absorbs visible light and transmits UV-light (UVA and UVB). Such filters are used for UV lighting applications.

Figure 6:
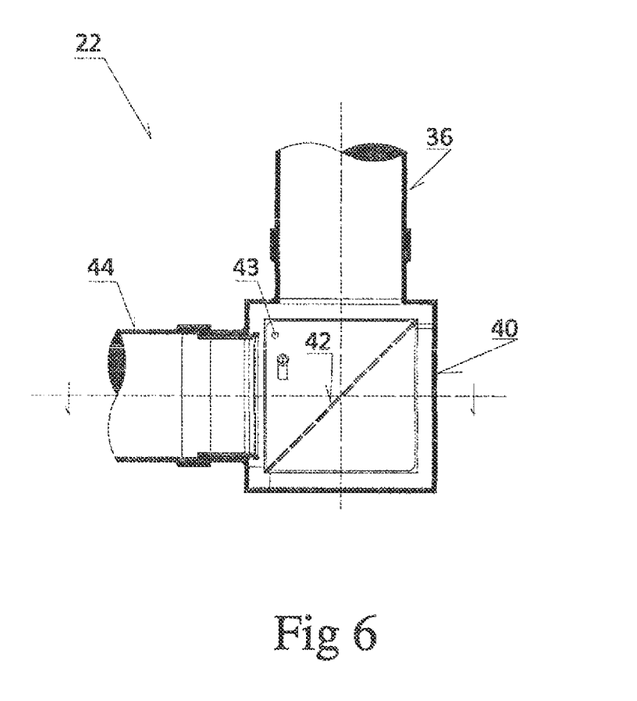
FIG. 6 shows a sectional elevation view A-A of a light transmission component for transmitting the light collected by the collector shown in FIGS. 2 to 4 to the interior of a room of the building shown in FIG. 1.
Figure 7:
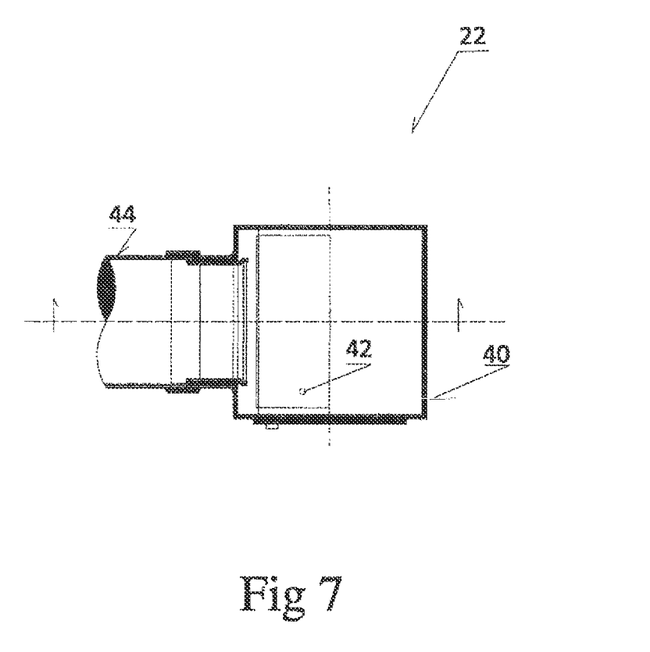
FIG. 7 shows a sectional plane view B-B of the light transmission component shown in FIG. 6.

The tube 36 (lightpipe) is made of PVC and covered from inside by highly polished aluminum sheet. The tube 36 has a length of 6000 mm. Further, as shown in FIGS. 1, 6 and 7, the light transmission component 22 comprises a 90 degree aluminum elbow 40. Said elbow 40 is box-shaped and contains a plane reflector 42 and may (also) contain a visible light filter. The elbow 40 also comprises a maintenance door 43. Said reflector 42 reflects/deflects the vertically propagating light into the horizontal direction. It may be made out of aluminum covered by highly polished aluminum sheet with the size of 24"×48" and a thickness of 0.02" for UV lamp reflectors.

Figure 8:
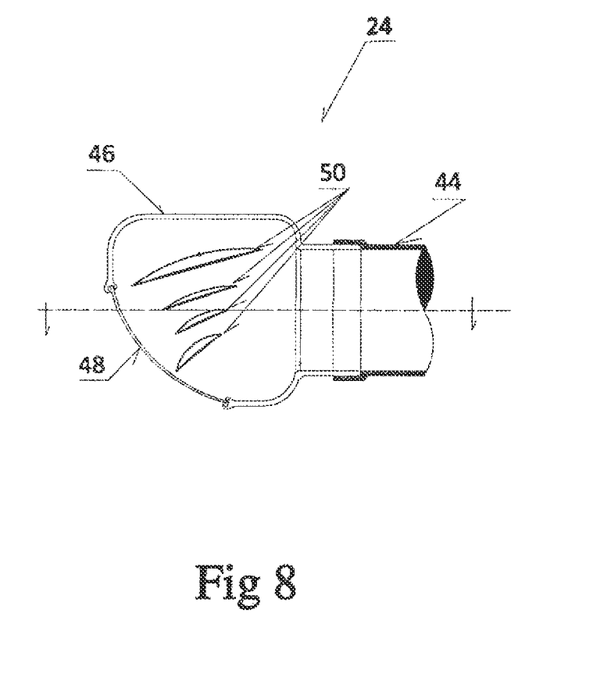
FIG. 8 shows a sectional elevation view A-A of a light distributor for distributing the UV-light over a square area of a room as part of the apparatus shown in FIG. 1.
Figure 9:
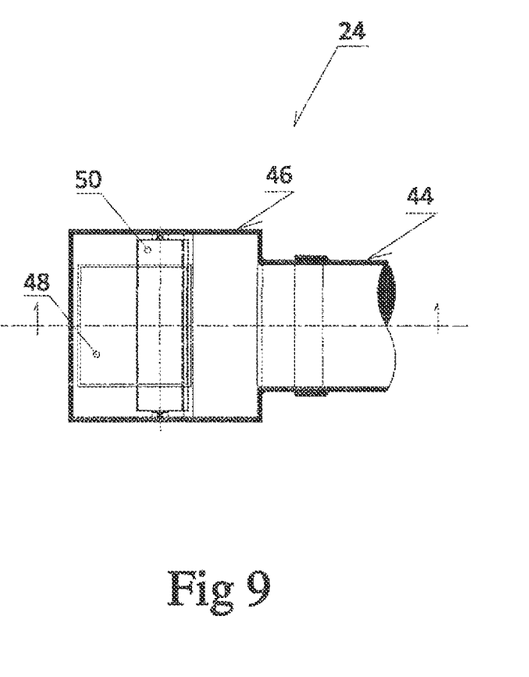
FIG. 9 shows a sectional plane view B-B of FIG. 8.

When leaving the elbow 40, the light is horizontally transmitted by a further tube 44 that may be made in the same way as the tube 36. At the end of said tube 44, the distributor 24 is arranged. It consists of a box 46 (s. FIG. 8) made of aluminum with a thickness of 4 mm. Said box 46 is covered by an anti-dust-anti-fog-plastic plate 48. Multiple micro-reflectors 50 are arranged within the box 46. Said reflectors distribute the light that leaves the tube 44. The light is distributed to the square area SA of the room 10. The reflectors 42 are made out of aluminum covered by highly polished aluminum sheet with a size of 24"×48" and a thickness of 0.02" used for UV lamp reflectors. The dimensions of the distributor 24 are: height 150 mm, length 150 mm and width 150 mm.

It should be understood that the apparatus described above could be modified, for example regarding a shape and dimensions of its components. Also, it could comprise a controller for controlling the UV-dosage and switching-off the UV-radiation when a predetermined UV-dosage is reached.

The apparatus described above is designed to catch the direct sunlight at the flat-roof 20 and dispersing the ultraviolet light indoor. The dispersion indoor amount of UVB is calculated as 200 times less than the direct source at transmission device efficiency of 50%. At clear sky the expected maximum UV index ranges from 6 to 10. The expected indoor UVB scale index ranges from 0.03 to 0.05. The expected dosage for staying for one hour using the apparatus is calculated as ranging from 360 to 600 IU. The current daily recommended dosage of vitamin D for adults with an age of 50 or older is 400 to 600 International Units (IU). But many researchers believe that a higher amount is warranted because of the many health benefits. The USA National Osteoporosis Foundation recommends a daily intake of 800 to 1.000 IU per day. Special designs could be made for school classrooms, kitchens, and bedrooms. The invention is to provide safe ultraviolet light into for example residential houses as well as into for example school classrooms and governmental offices. The apparatus will protect users from being subjected to extreme heat during exposing to direct sunlight seeking UV-light. The apparatus prohibits dust, insects, flies, smells, heat and event sunlight going through.

The features disclosed in the foregoing description, in the claims and/or in the accompanying drawings may, both separately and in any combination thereof, be material for realising the invention in diverse forms thereof.

REFERENCE LIST

10 Room
12 House
14 Apparatus
16 Façade
18 Collector
20 Roof
22 Light transmission component
24 Distributor
26 Bottom box
28 Multiple reflector dish antenna
30 Top box
32 Multiple sub-reflector
34 Anti-dust-anti-fog-plastic plate
36 Tube
38 Visible light filter
40 Elbow
42 Plane reflector
43 Maintenance door
44 Tube
46 Box
48 Anti-dust-anti-fog-plastic plate
50 Micro-reflectors
SA Square Area
CSA Collector Square Area

The invention claimed is:

1. A UV light therapy apparatus for treatment of vitamin D deficiency, comprising:
a stationary daylight and/or sunlight collector comprising a multiple reflector antenna for collecting daylight and/or sunlight over a collector square area (CSA),
a light pipe for transmitting the light collected by the collector to the interior of a room of a residential house, wherein the light pipe is a single tube covered on its inner surface by polished aluminum,
an optical filter that absorbs visible light and transmits only UV-light included in the daylight and/or sunlight and is arranged within the collector, and
a light distributor for distributing the UV-light transmitted by the optical filter over a square area (SA) of the room, wherein the square area (SA) is all of the room square area (SA) and larger than the collector square area (CSA),
wherein the ratio of the collector square area CSA and the square area SA of the room is such that the UVB scale index ranges from about 0.03 to about 0.05 in the room when the UVB scale index ranges from about 6 to about 10 outside of the residential house,
wherein the multiple reflector antenna comprises a multiple reflector dish antenna configured to reflect the daylight and/or sunlight to a multiple sub reflector, and the multiple sub reflector is configured to send the daylight and/or sunlight into the light pipe and to the optical filter, and wherein the multiple reflectors partially overlap such that a portion of each reflector is occluded by an adjacent reflector.

2. The apparatus according to claim 1 characterized in that the light transmission component comprises a deflecting means for deflecting the light.

3. The apparatus according to claim 2 characterized in that the deflecting means deflects light in a horizontal direction.

4. The apparatus according to claim 3 further comprising a horizontally oriented light pipe that transmits the light in the horizontal direction.

5. The apparatus according to claim 1 characterized in that the light distributor comprises one or more optical microreflectors.

6. The apparatus according to claim 1 characterized in that it comprises a controller for controlling the UV-dosage and switching-off the UV-radiation when a predetermined UV-dosage is reached.

7. A building comprising at least one of the apparatus according to claim 1.

8. The apparatus according to claim 1 wherein the light pipe is a UV-light pipe.

9. The apparatus according to claim 1 wherein the light pipe is a vertically extending light pipe.

10. The apparatus according to claim 1, wherein the light distributor is configured to directly distribute the UV-light transmitted by the optical filter over all of the room square area, wherein the room is a kitchen in the residential house.

11. The apparatus according to claim 1 wherein the multiple reflector dish antenna has a dish parabolic diameter and the multiple sub reflector has a reflector parabolic diameter, and the ratio of the dish parabolic diameter to the reflector parabolic diameter is about 5/1.

12. A UV light therapy apparatus for treatment of vitamin D deficiency, comprising:
a stationary daylight and/or sunlight collector comprising a multiple reflector antenna for collecting daylight and/or sunlight over a collector square area (CSA),
a light pipe for transmitting the light collected by the collector to the interior of a room of a residential house, wherein the light pipe is a single tube covered on its inner surface by polished aluminum,
an optical filter that absorbs visible light and transmits only UV-light included in the daylight and/or sunlight and is arranged within the collector, and
a light distributor for distributing the UV-light transmitted by the optical filter over a square area (SA) of the room, wherein the square area (SA) is all of the room square area (SA) and larger than the collector square area (CSA), wherein the ratio of the collector square area CSA and the square area SA of the room is such that the UVB scale index ranges from about 0.03 to about 0.05 in the room when the UVB scale index ranges from about 6 to about 10 outside of the residential house, wherein the multiple reflector antenna comprises a multiple reflector dish antenna configured to reflect the daylight and/or sunlight to a multiple sub reflector, and wherein the multiple reflectors partially overlap such that a portion of each reflector is occluded by an adjacent reflector, and the multiple sub reflector is configured to send the daylight and/or sunlight into the light pipe and to the optical filter, and wherein the light pipe is a vertically extending UV-light pipe.

13. The apparatus according to claim 12 characterized in that the light transmission component comprises a deflecting means for deflecting the light.

14. The apparatus according to claim 12 characterized in that the light distributor comprises one or more optical micro-reflectors.

15. The apparatus according to claim 12 characterized in that the apparatus further comprises a controller for controlling the UV-dosage and switching-off the UV-radiation when a predetermined UV-dosage is reached.

16. A building comprising at least one of the apparatus according to claim 12.

17. The apparatus according to claim 12 wherein the multiple reflector dish antenna has a dish parabolic diameter and the multiple sub reflector has a reflector parabolic diameter, and the ratio of the dish parabolic diameter to the reflector parabolic diameter is about 5/1.

* * * * *